United States Patent [19]
Andrae et al.

[11] Patent Number: 5,583,690
[45] Date of Patent: Dec. 10, 1996

[54] FARADAY MICROSCOPE WITH MAGNETO-OPTICAL INDICATOR AS TERMINATING ELEMENT OF OBJECTIVE LENS

[75] Inventors: Wilfried Andrae; Peter Goernert, both of Jena; Rudolf Hergt, Apolda; Jochen Taubert, Jena; Karl-Heinz Geier, Jena; Lothar Schreiber, Jena; Reed Werlich, Jena, all of Germany

[73] Assignee: Carl Zeiss Jena GmbH, Jena, Germany

[21] Appl. No.: 379,318

[22] Filed: Jan. 25, 1995

[30] Foreign Application Priority Data

Jan. 25, 1994 [DE] Germany ............................ 44 02 059.7

[51] Int. Cl.$^6$ .................................................. G02B 21/00
[52] U.S. Cl. .................................... 359/368; 359/484
[58] Field of Search ................................ 359/368, 371, 359/382, 383, 385, 386, 484, 488, 494, 656

[56] References Cited

U.S. PATENT DOCUMENTS 5,420,717  5/1995  Tabata ...................................... 359/371

Primary Examiner—Timothy P. Callahan
Assistant Examiner—Jeffrey Zweizig
Attorney, Agent, or Firm—McAulay Fisher Nissen Goldberg & Kiel, LLP

[57] ABSTRACT

In a Faraday microscope for examining specimens with stray magnetic fields in a reflected light beam path with a magnetic indicator film arranged in front of the specimen, the influence of the specimen on the indicator film is evaluated with the indicator film arranged as the termination of the microscope objective, the indicator film advantageously being arranged on an optically transparent substrate. The indicator film and substrate are taken into account in the optical calculation of the microscope objective.

26 Claims, 3 Drawing Sheets

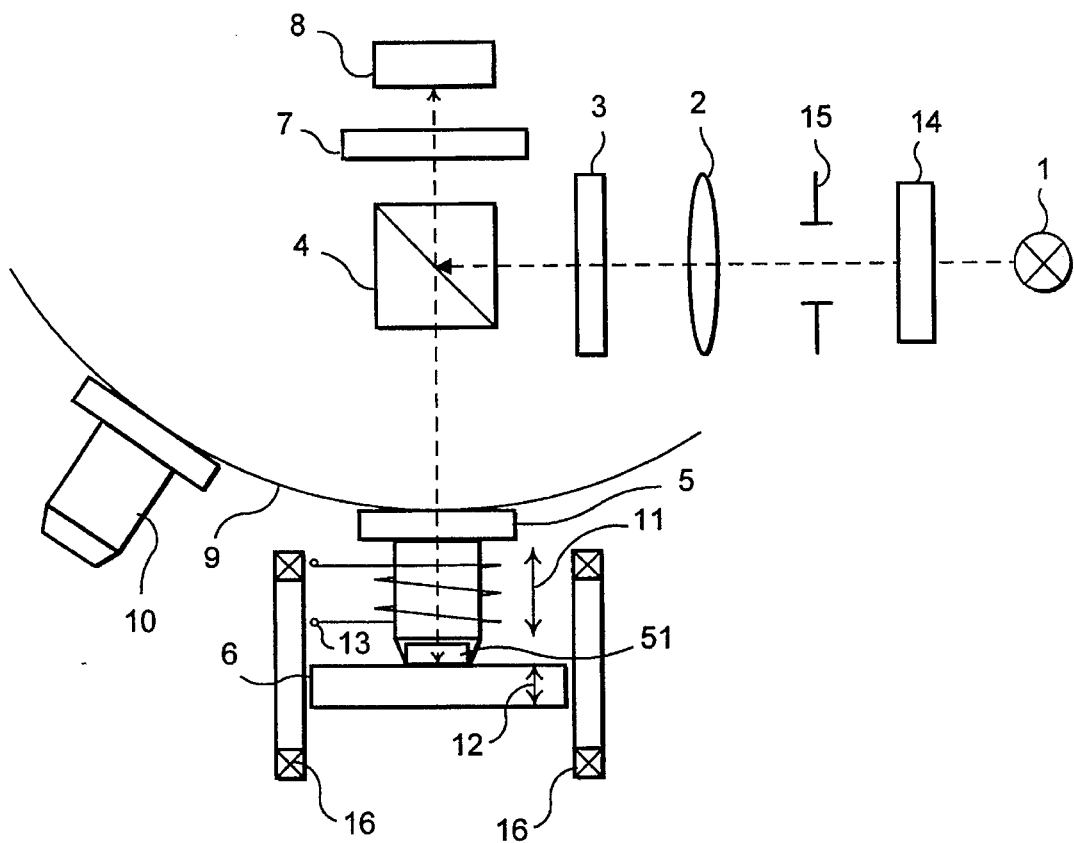
F I G. 1
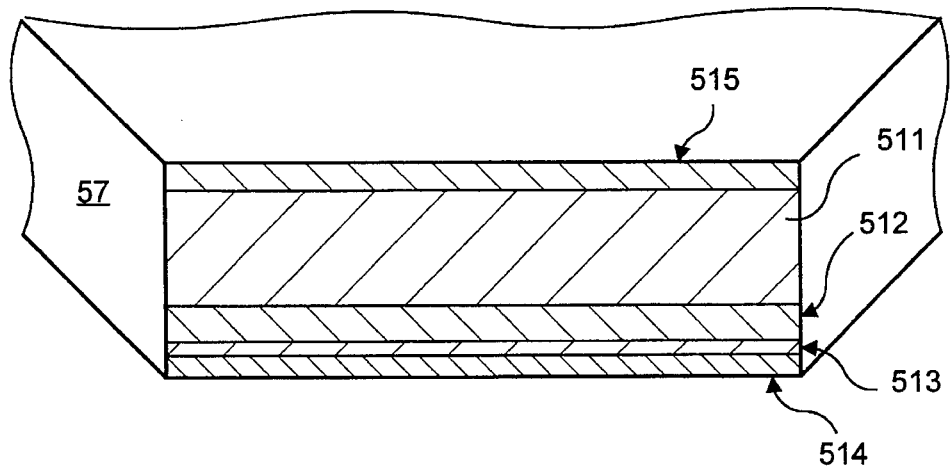
F I G. 3

FARADAY MICROSCOPE WITH MAGNETO-OPTICAL INDICATOR AS TERMINATING ELEMENT OF OBJECTIVE LENS

BACKGROUND OF THE INVENTION

1. Field of the Invention

The invention is directed to a Faraday microscope for examining specimens with stray magnetic fields in a reflected light beam path, wherein a magneto-optical film is arranged in front of the specimen and the influence of the specimen on the indicator film is evaluated with respect to optical polarization, and to a process for adjusting the Faraday microscope.

2. Background of the Invention

Arrangements of this type are known from (1) B. Ludescher, et al., "Faraday Low-Temperature Microscope for Observing Dynamic Magnetization Processes in Superconductors [Faraday-Tieftemperatur-Mikroskop zur Beobachtung dynamischer Magnetisierungsvorgänge in Supraleitern]", *Laser und Optoelektronik* 23 (1991), pages 54–58; (2) L. A. Dorosinskii, et al., *Physica C* 203 (1992), page 149; (3) M. V. Indenbohm, et al., *Physica C* 209 (1993), page 295.

A device for detecting magneto-optical anisotropism, particularly of magnetic recording media, is described in U.S. Pat. No. 4,410,227.

A laser polarizing microscope for observing magnetic domains is known from JP 3-185338 (A).

A Kerr microscope for examining current paths utilizing the polar Kerr effect is known from DE 4027049.

The magneto-optical Faraday effect causes a rotation of the polarization plane of polarized light at angle w as it passes through a magneto-optical material of thickness d according to the equation $$w=RM(x)d,$$

where R represents a material constant of the magneto-optical material and $M(x)$ represents the magnetization component at point x parallel to the light path.

The rotation of the plane of polarization is visible by observing the light at the polarizer-analyzer intersection. For example, with the aid of the Faraday effect, dynamic processes in superconductors and magnetic structures in magnetic storage media can be examined. In general, the constant R is so small that the Faraday effect is observed only in special materials.

A "Faraday microscope" in which a magneto-optically active film is vacuum-deposited on the superconductor to be examined is known (see 1 above). Since the Faraday rotation which can be achieved is very small, the interference between the light beams reflected at the surface of the magneto-optical film and those reflected in regions at the surface of the superconductor which are free of magnetic fields is used for evaluation. It is disadvantageous that every specimen to be analyzed must first be vacuum-deposited.

It is known (see 2, 3 above) to place thin magneto-optical indicator plates on the specimen to be analyzed, since the lateral resolution and sensitivity of the indicator decreases sharply with increasing distance from the specimen. In so doing, there is a risk that the specimen will be scratched. Moreover, a large indicator plate must be used when analyzing specimens extending over a surface area in order to avoid repeated placement. However, large indicator plates are expensive and difficult to produce. The indicator plate is formed by a substrate (garnet) on which the actual magneto-optical indicator film has been deposited. The substrate has a high index of refraction (n=approximately 2) so that the optical imaging is impaired when observing the magneto-optical indicator film.

OBJECT AND SUMMARY OF THE INVENTION

The primary object of the present invention is to realize an improved Faraday microscope for examining specimens with stray magnetic fields. In particular, damage to the surface of specimens is substantially prevented and different specimens may be examined. Further, the invention makes it possible to bring the indicator film as close as possible to the analyzed region of the surface of the specimen which is generally not perfectly planar.

According to the invention, this object is met in a Faraday microscope for examining specimens with stray magnetic fields in a reflected-light beam path, wherein a magneto-optical indicator film is arranged in front of the specimen and the influence of the specimen on the indicator film is evaluated with respect to optical polarization, the improvement comprising that the indicator film is arranged at the end of a microscope objective. Preferred further embodiments and an adjustment process for the microscope objective are within the scope of the invention. A preferred embodiment of a microscope objective is also within the scope of the invention.

A strain-free, (reflected-light) microscope objective suitable for polarization and having a magneto-optical indictor plate as its terminating element is particularly advantageous. The indicator plate is taken into account in the optical calculation for the microscope objective. Further, the objective has an arrangement for protecting the specimen and objective.

Operation of this objective is further facilitated by the use of automatic focussing. In so doing, focussing on the specimen is first effected automatically by a different objective with a reduced depth of field, the location on the object to be examined is selected, whereupon the objective with the indicator plate is switched to. The focussing device now automatically moves the objective with the indicator plate to a minimum distance from the specimen. For this purpose, it is necessary to determine and store the difference between the balanced length of the objective with the reduced depth of field and that of the objective with the indicator plate in an adjustment process following assembly of the microscope.

The indicator plate normally has a reflective layer. A transparent indicator plate without a reflective layer can also be used in an advantageous manner with favorably reflecting, optically isotropic specimens. The specimen can be observed first without a polarizer so that a bright-field image is achieved. When the polarizer/analyzer is switched on, an imaging of the magnetic properties of the specimen is achieved. In this way, a correlation between the surface structure of the specimen and magnetic field contrast is made possible without the use of an additional objective.

When highly reflective optically isotropic specimens are used, the indicator plate can also advantageously have a semi-transparent reflective layer. The semi-transparent reflective layer can be used in the bright field without polarizers for interferometric adjustment of the distance between the indicator plate and the surface of the specimen. The interference can also be used to detect the correlation between surface topology and magnetic contrast when a polarizer/analyzer is used.

Further, the objective according to the invention is advantageously surrounded by a current coil or Helmholtz coil. A magnetic field (along the optical axis) can be generated and modulated with the current coil, which can be used to improve contrast (e.g., elimination of earth field) and to influence the specimen in situ. A magnetic field can be produced vertically to the optical axis with a Helmholtz coil to homogenize the indicator plate.

Further, the microscope is advantageously outfitted with a monochromator (e.g., exchangeable interference filters) to make use of the dispersion of the Faraday rotation.

Further, the microscope advantageously has an aperture stop which is adjustable vertically to the optical axis so that in-plane magnetization components of the specimen can also be detected by oblique incidence of light with eccentric aperture stop.

The invention is explained more fully in the following with reference to the schematic drawings.

BRIEF DESCRIPTION OF THE DRAWINGS

In the drawings:

FIG. 1 illustrates a schematic construction of a microscope according to the invention;

FIG. 3 illustrates a variant of an indicator plate in accordance with the invention.

DESCRIPTION OF THE PREFERRED EMBODIMENTS

Figure 2:
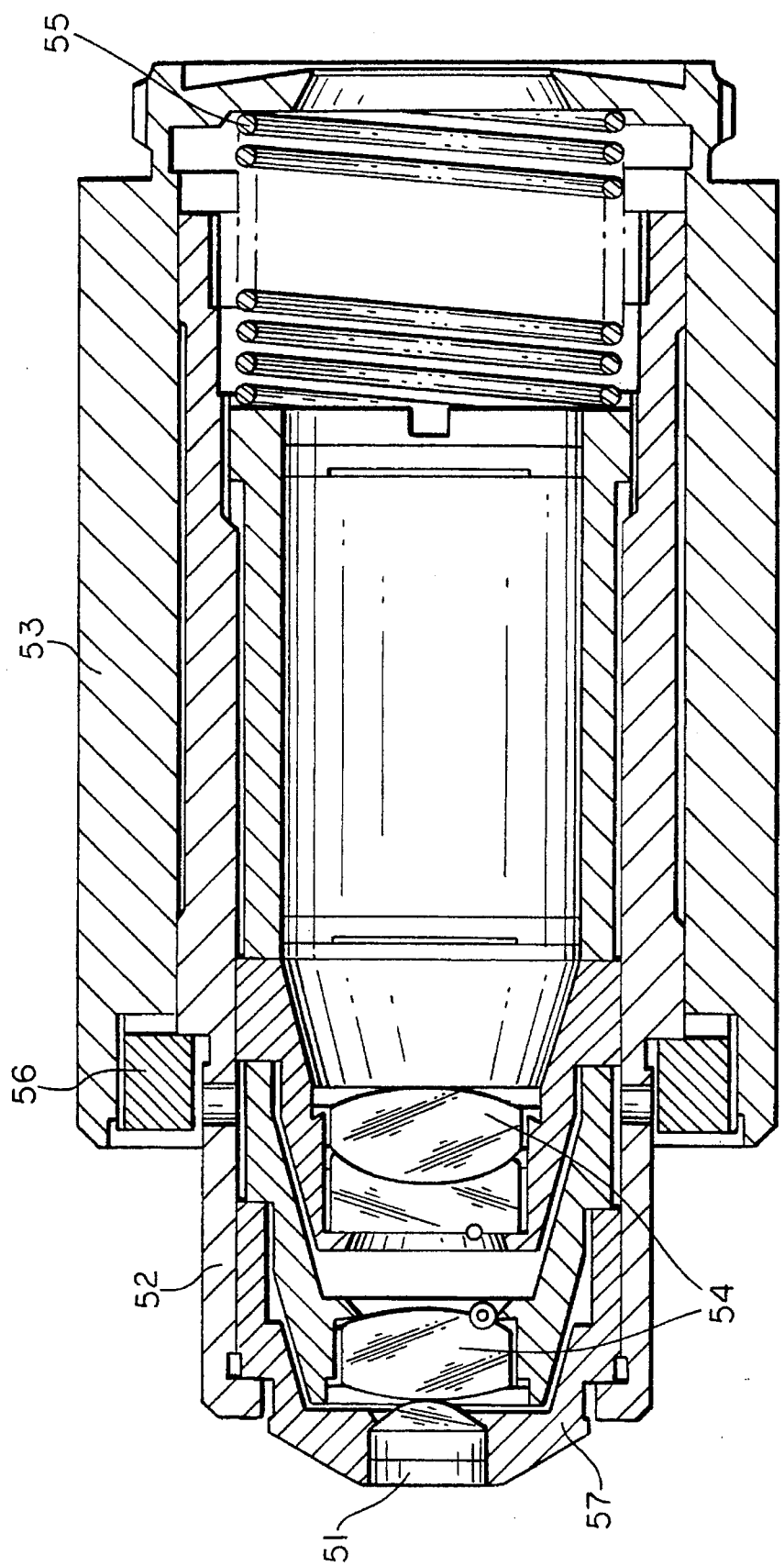
FIG. 2 illustrates a diagram of the objective according to the invention.

The general construction of the microscope according to the invention is shown schematically in FIG. 1. The light from a light source 1 with associated illuminating optics 2 is linearly polarized in a polarizer 3. A deflecting element or beam splitter 4 deflects the light into the objective 5 according to the invention. A Berek prism is advantageously provided as beam splitter, since this ensures a homogeneous polarization field with high-intensity illumination and, accordingly, optimal contrast can be achieved at light intensities which are frequently low.

Due to its magnetic field components, the magnetic specimen 6 causes a rotation of the plane of polarization of light in the indicator plate 51. The light is reflected at the reflective layer of the indicator plate 51, passes through the objective and reaches the analyzer 7 via the beam splitter. If the analyzer 7 is crossed with the polarizer 3, light only enters through the analyzer when a Faraday rotation has taken place. Accordingly, the light which reaches the video camera 8 or is observed visually via imaging optics contains an image of the magnetic characteristics of the specimen.

One or both of the polars are advantageously constructed so as to be rotatable so as to enable variation in contrast.

The construction of the objective according to the invention is shown schematically in FIG. 2. The objective contains the indicator plate 51 as terminating element. The entire lens system 54 including the indicator plate 51 is arranged in a sliding tube 52. The sliding tube 52 is guided in a stationary tube 53 and is pressed against a stop 56 by a spring 55. This arrangement protects the specimen and objective and ensures contact between the indicator plate and specimen. The front barrel or mount 57 can be produced from a softer material, e.g., Teflon.

A variant of the construction of the indicator plate 51 is shown schematically in FIG. 3. The magneto-optical film 512 is deposited on a suitable, often monocrystalline, substrate 511 followed by a reflective layer 513 which is protected by a protective layer 514. Another advantage of the reflective layer consists in that the light passes twice through the magneto-optical indicator film so that the rotation of the plane of polarization is doubled. The objective 5 is so dimensioned in the optics calculation that the object plane lies in the reflective layer.

The indicator plate advantageously supports an anti-reflection coating 515 because the substrate often has a high refractive index and accordingly high inherent reflection. The anti-reflection coating 515 improves contrast.

When highly reflective, optically isotropic specimens are used, the indicator plate can also advantageously have a semi-transparent reflective layer 513. The semi-transparent reflective layer can be used in the bright field without polarizer 2 for interferometric adjustment of the distance between the indicator plate and the surface of the specimen. The interference can also be used to detect the correlation between surface topology and magnetic contrast when the polarizer/analyzer is switched on.

Further, the objective 5 according to the invention is advantageously surrounded by a small current coil 13. A magnetic field can be generated along the optical axis and modulated with the current coil, which can be used to improve contrast (e.g., elimination of earth field) and to influence the specimen in situ. A magnetic field can be produced vertically to the optical axis, i.e., parallel to the surface of the specimen, with a Helmholtz coil 16 which can be used to homogenize the indicator plate. If the microscope is equipped with automatic focussing acting on the objective focussing arrangement 11 or stage focussing arrangement 12, the difference between the balanced length of the objective 10 with reduced depth of field and that of the objective 5 with the indicator plate is first determined and stored in an adjustment process following assembly of the microscope. Then, focussing on the specimen is first effected automatically by the objective 10 with reduced depth of field, the location on the object to be examined is selected, and the objective turret 9 is switched to the objective 5 with indicator plate. The focussing device now automatically moves the objective 5 with indicator plate to the minimum optimum distance from the specimen.

The microscope is advantageously outfitted with a monochromator 14 (e.g., exchangeable interference filters) to make use of the dispersion of the Faraday rotation. Accordingly, the wavelength at which the magneto-optical film 512 has its maximum Faraday rotation can be used.

Further, the microscope advantageously has an aperture stop 15 which is adjustable vertically to the optical axis so that in-plane magnetization components of the specimen can also be detected by oblique incident light with eccentric aperture stop.

Figure 4:
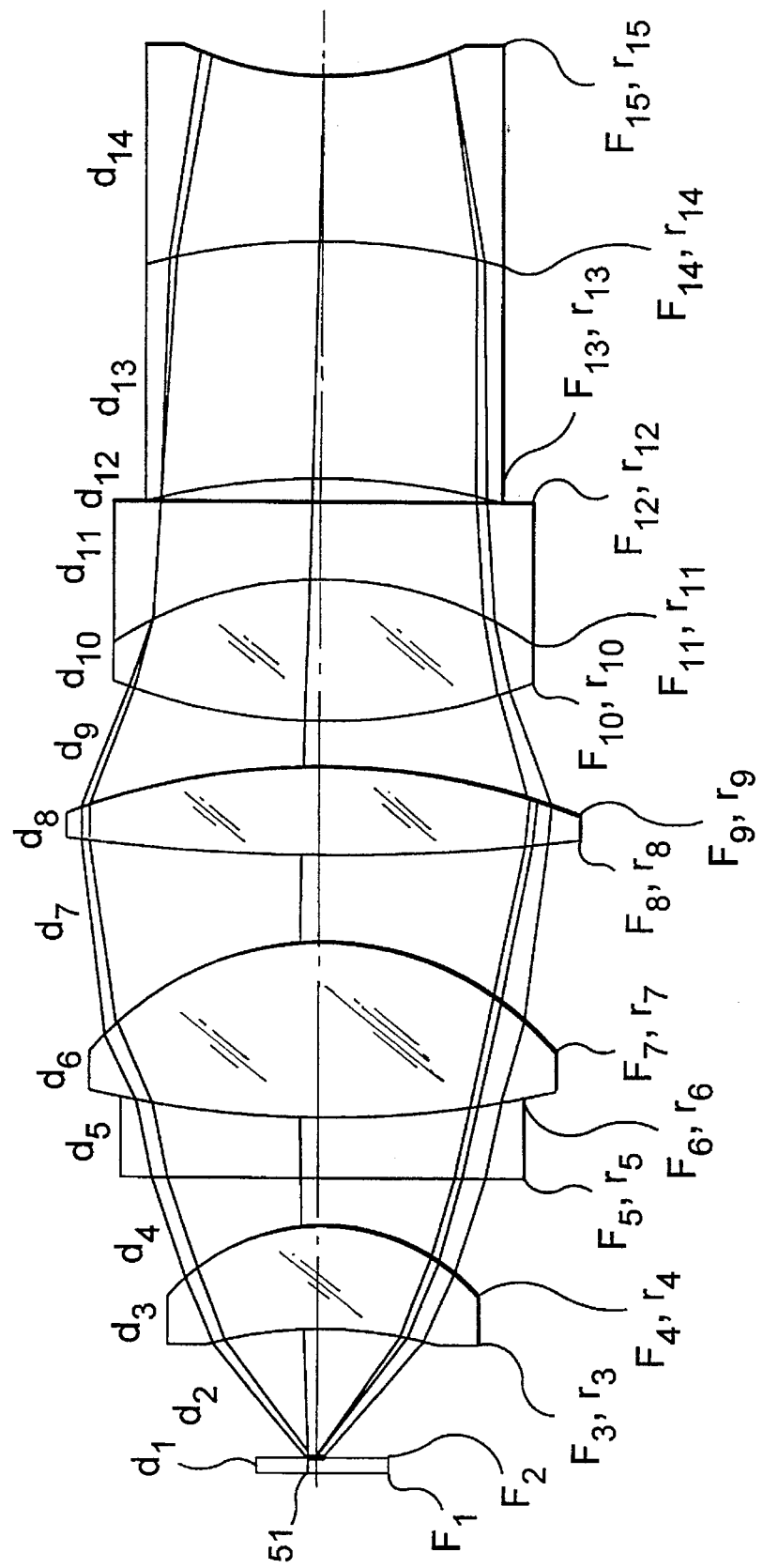
FIG. 4 illustrates an example of a microscope with integrated indicator plate.

FIG. 4 shows an advantageous example of a microscope objective with integrated indicator plate with surfaces F1, F2 and lens surfaces F3–F15 with distances d1–d14 and radii of curvature r1–r15. The optical parameters are:

| Surface no. | Radius | Distance | Glass type | Refractive index |
|---|---|---|---|---|
| 1 | infinite | | | 1.0000 |
| | | 0.50000 | garnet | 1.9740 |
| 2 | infinite | 4.33505 | | 1.0000 |
| 3 | −18.73716 | 3.29010 | psk1 | 1.54979 |
| 4 | −7.25655 | 1.50822 | | 1.0000 |
| 5 | 392.44918 | 1.50000 | sf4 | 1.761670 |
| 6 | 18.64128 | 6.00000 | fk51 | 1.48794 |
| 7 | −11.16745 | 3.70000 | | 1.00000 |
| 8 | 56.63752 | 2.95000 | lask3 | 1.734438 |
| 9 | −21.36052 | 1.77000 | | 1.00000 |
| 10 | 19.47278 | 4.80000 | fk51 | 1.48794 |
| 11 | −11.12580 | 2.500000 | sf4 | 1.76167 |
| 12 | −664.96261 | 0.75000 | | 1.00000 |
| 13 | −21.41133 | 8.25000 | sf4 | 1.76167 |
| 14 | −9.30821 | 5.35000 | bk3 | 1.500140 |
| 15 | 9.88940 | | | | within a tolerance of 20%.

While the foregoing description and drawings represent the preferred embodiments of the present invention, it will be obvious to those skilled in the art that various changes and modifications may be made therein without departing from the true spirit and scope of the present invention.

What is claimed is:

1. In a Faraday microscope for examining specimens with stray magnetic fields in a reflected-light beam path, wherein a magneto-optical indicator film is arranged in front of the specimen and the influence of the specimen on the indicator film is evaluated with respect to optical polarization, the improvement comprising that the indicator film is arranged at the end of a microscope objective as a terminating element of said objective.

2. The Faraday microscope according to claim 1, wherein the indicator film is arranged on an optically transparent supporting substrate, the indicator film and substrate being taken into account in the optical calculation of the microscope objective.

3. The Faraday microscope according to claim 2, wherein the indicator film is a component part of an indicator plate which is arranged along with the optical elements of the microscope objective in a common housing.

4. The Faraday microscope according to claim 3, wherein the indicator plate is provided with a protective layer in the direction of the specimen.

5. The Faraday microscope according to claim 2, wherein an anti-reflection coating is provided in front of the supporting substrate in the direction of light.

6. The Faraday microscope according to claim 1, wherein an anti-reflection coating is provided subsequent to the indicator film in the direction of light.

7. The Faraday microscope according to claim 4, wherein the protective layer is formed as an anti-reflection coating.

8. The Faraday microscope according to claim 2, wherein the supporting substrate is a monocrystalline substrate.

9. The Faraday microscope according to claim 1, wherein a reflective layer is arranged subsequent to the indicator film in the direction of light.

10. The Faraday microscope according to claim 9, wherein the reflective layer is arranged between the indicator film and the protective layer.

11. The Faraday microscope according to claim 9, wherein the reflective layer is semi-transparent.

12. The Faraday microscope according to claim 1, wherein the microscope objective with the indicator film is arranged in a sliding tube which is guided in an outer tube so as to be displaceable.

13. The Faraday microscope according to claim 12, wherein the sliding tube is supported in a springing manner and its displacement is limited by a stop.

14. The Faraday microscope according to claim 3, wherein a crossed polarizer/analyzer arrangement is provided for detecting rotation of the polarization plane by the indicator plate, at least one of the polars being rotatable for the purpose of variation in contrast.

15. The Faraday microscope according to claim 3, wherein the indicator plate is arranged in the immediate vicinity of the specimen.

16. The Faraday microscope according to claim 3, wherein the indicator plate is placed on the specimen.

17. The Faraday microscope according to claim 1, including means for providing a magnetic field in the vicinity of the microscope objective to influence the magnetic properties of the specimen.

18. The Faraday microscope according to claim 17, wherein the microscope objective is surrounded by said means which includes a current-conducting coil for generating a magnetic field parallel to the optical axis.

19. The Faraday microscope according to claim 17, said means for providing a magnetic field includes a Helmholtz coil, said field being generated vertically to the optical axis.

20. The Faraday microscope according to claim 19, wherein a monochromator with adjustable wavelength is provided in the optical path of the microscope.

21. The Faraday microscope according to claim 1, wherein an adjustable aperture stop is provided in the beam path.

22. The Faraday microscope according to claim 1, wherein the illuminating beam path and the analysis beam path are united via a beam splitter.

23. The Faraday microscope according to claim 22, wherein the beam splitter is a Berek prism.

24. The Faraday microscope according to claim 1, wherein said microscope objective has the following optical parameters with lens surfaces with surface numbers 3–15 and distances d1–d14 and wherein an indicator plate is arranged in front of the objective with surface numbers 1 and 2:

| Surface no. | Radius (mm) | Distance d (mm) | Glass type | Refractive index |
|---|---|---|---|---|
| 1 | infinite | | | 1.0000 |
| | | 0.50000 | garnet | 1.9740 |
| 2 | infinite | 4.33505 | | 1.0000 |
| 3 | −18.73716 | 3.29010 | psk1 | 1.54979 |
| 4 | −7.25655 | 1.50822 | | 1.0000 |
| 5 | 392.44918 | 1.50000 | sf4 | 1.761670 |
| 6 | 18.64128 | 6.00000 | fk51 | 1.48794 |
| 7 | −11.16745 | 3.70000 | | 1.00000 |
| 8 | 56.63752 | 2.95000 | lask3 | 1.734438 |
| 9 | −21.36052 | 1.77000 | | 1.00000 |
| 10 | 19.47278 | 4.80000 | fk51 | 1.48794 |
| 11 | −11.12580 | 2.500000 | sf4 | 1.76167 |
| 12 | −664.96261 | 0.75000 | | 1.00000 |
| 13 | −21.41133 | 8.25000 | sf4 | 1.76167 |
| 14 | −9.30821 | 5.35000 | bk3 | 1.500140 |
| 15 | 9.88940 | | | | within a tolerance of 20%.

25. A process for adjusting a Faraday microscope objective with integrated indicator plate relative to the surface of a superconducting specimen, comprising the steps of: focusing a different objective with reduced depth of field on the specimen surface in a first step, and placing the microscope objective with integrated indicator plate in the beam path and adjusting the objective to a minimum distance from the specimen in a second step.

26. The process according to claim 25, including the step of determining the difference between the balanced length of the objective with reduced depth of field and that of the objective with integrated indicator plate during adjustment and taking said differences into account when setting the minimum distance from the specimen.

* * * * *